(12) United States Patent
Sullivan et al.

(10) Patent No.: US 11,969,607 B2
(45) Date of Patent: *Apr. 30, 2024

(54) WEARABLE CARDIOVERTER DEFIBRILLATOR (WCD) WITH POWER-SAVING FUNCTION

(71) Applicant: WEST AFFUM HOLDINGS DAC, Dublin (IE)

(72) Inventors: Joseph L. Sullivan, Kirkland, WA (US); Jaeho Kim, Redmond, WA (US)

(73) Assignee: West Affum Holdings DAC, Dublin (IE)

( * ) Notice: Subject to any disclaimer, the term of this patent is extended or adjusted under 35 U.S.C. 154(b) by 437 days.

This patent is subject to a terminal disclaimer.

(21) Appl. No.: 17/194,871

(22) Filed: Mar. 8, 2021

(65) Prior Publication Data
US 2021/0187312 A1 Jun. 24, 2021

Related U.S. Application Data

(63) Continuation of application No. 15/715,500, filed on Sep. 26, 2017, now Pat. No. 10,940,323.
(Continued)

(51) Int. Cl.
*A61N 1/39* (2006.01)
*A61B 5/00* (2006.01)
(Continued)

(52) U.S. Cl.
CPC .......... *A61N 1/3987* (2013.01); *A61B 5/0205* (2013.01); *A61B 5/361* (2021.01);
(Continued)

(58) Field of Classification Search
CPC .. A61N 1/3987; A61N 1/0484; A61N 1/3975; A61N 1/3904; A61N 1/3956;
(Continued)

(56) References Cited

U.S. PATENT DOCUMENTS 3,724,355 A 4/1973 Unger
4,583,524 A 4/1986 Hutchins
(Continued)

FOREIGN PATENT DOCUMENTS

DE 102005060985 A2 6/2007
EP 2305110 B1 4/2018
(Continued)

OTHER PUBLICATIONS

Zoll, LifeVest, Proven protection from Sudden Cardiac Death, issued Mar. 27, 2018, 4 pages. Pittsburgh PA, USA.
(Continued)

*Primary Examiner* — Aaron F Roane
(74) *Attorney, Agent, or Firm* — Christensen O'Connor Johnson Kindness PLLC

(57) ABSTRACT

A Wearable Cardioverter Defibrillator (WCD) system has a processor that performs two different analyses to an ECG of the patient. A first-level analysis can be computationally economical, while a fuller second-level analysis can give shock/no-shock advice with more certainty. In some of these embodiments the second-level analysis of the ECG is performed only if the first-level analysis of the ECG detects a possible shockable condition. As such, the first-level analysis may operate as a gatekeeping function, often preventing the more computationally intensive second-level analysis from being performed. An advantage can be that the WCD system needs to store less charge, for powering the processor. In turn, this permits portions of the WCD system to be less bulky and weigh less.

30 Claims, 9 Drawing Sheets

SAMPLE COMPONENTS OF WEARABLE
CARDIOVERTER DEFIBRILLATOR (WCD)
SYSTEM

Related U.S. Application Data

(60) Provisional application No. 62/404,158, filed on Oct. 4, 2016.

(51) Int. Cl.
| | |
|---|---|
| *A61B 5/0205* | (2006.01) |
| *A61B 5/361* | (2021.01) |
| *A61B 5/363* | (2021.01) |
| *A61N 1/04* | (2006.01) |
| *A61B 5/11* | (2006.01) |

(52) U.S. Cl.
CPC ............ *A61B 5/363* (2021.01); *A61B 5/4836* (2013.01); *A61N 1/0484* (2013.01); *A61N 1/3975* (2013.01); *A61B 5/1118* (2013.01); *A61B 5/6805* (2013.01); *A61B 5/6823* (2013.01); *A61N 1/3904* (2017.08); *A61N 1/3956* (2013.01); *A61N 1/3968* (2013.01)

(58) Field of Classification Search
CPC ...... A61N 1/3968; A61B 5/361; A61B 5/363; A61B 5/0205; A61B 5/4836; A61B 5/1118; A61B 5/6805; A61B 5/6823
USPC .......................................................... 607/5
See application file for complete search history.

(56) References Cited

U.S. PATENT DOCUMENTS

| | | |
|---|---|---|
| 4,619,265 A | 10/1986 | Morgan et al. |
| 4,666,432 A | 5/1987 | McNeish et al. |
| 4,698,848 A | 10/1987 | Buckley |
| 4,928,690 A | 5/1990 | Heilman et al. |
| 4,955,381 A | 9/1990 | Way et al. |
| 5,078,134 A | 1/1992 | Hellman et al. |
| 5,228,449 A | 7/1993 | Christ et al. |
| 5,348,008 A | 9/1994 | Bomn et al. |
| 5,353,793 A | 10/1994 | Bomn |
| RE34,800 E | 11/1994 | Hutchins |
| 5,394,892 A | 3/1995 | Kenny |
| 5,405,362 A | 4/1995 | Kramer et al. |
| 5,429,593 A | 7/1995 | Matory |
| 5,474,574 A | 12/1995 | Payne et al. |
| 5,618,208 A | 4/1997 | Crouse et al. |
| 5,662,690 A | 9/1997 | Cole et al. |
| 5,708,978 A | 1/1998 | Johnsrud |
| 5,741,306 A | 4/1998 | Glegyak et al. |
| 5,782,878 A | 7/1998 | Morgan et al. |
| 5,792,204 A | 8/1998 | Snell |
| 5,902,249 A | 5/1999 | Lysler |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,280,461 B1 | 8/2001 | Glegyak et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 8/2002 | Brack et al. |
| 6,450,942 B1 | 9/2002 | Lapanashvili et al. |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,753,759 B2 | 7/2010 | Pintor et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 10/2012 | Donnelly et al. |
| 8,369,944 B2 | 2/2013 | Macho et al. |
| 8,527,028 B2 | 9/2013 | Kurzweil et al. |
| 8,548,557 B2 | 10/2013 | Garstka et al. |
| 8,560,044 B2 | 10/2013 | Kurzweil et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,706,255 B2 | 4/2014 | Phillips et al. |
| 8,742,349 B2 | 6/2014 | Urbon |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,084,583 B2 | 7/2015 | Mazar et al. |
| 9,089,685 B2 | 7/2015 | Sullivan et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,265,432 B2 | 2/2016 | Warren et al. |
| 9,345,898 B2 | 5/2016 | Piha et al. |
| 9,408,548 B2 | 8/2016 | Volpe et al. |
| 9,445,719 B2 | 9/2016 | Libbus et al. |
| 9,454,219 B2 | 9/2016 | Volpe et al. |
| 9,579,020 B2 | 2/2017 | Libbus et al. |
| 9,591,983 B2 | 3/2017 | Amir et al. |
| 9,592,403 B2 | 3/2017 | Sullivan |
| 9,598,799 B2 | 3/2017 | Shoshani et al. |
| 9,675,804 B2 | 6/2017 | Whiting et al. |
| 9,878,171 B2 | 1/2018 | Kaib |
| 9,895,105 B2 | 2/2018 | Romem |
| 9,901,741 B2 | 2/2018 | Chapman et al. |
| RE46,926 E | 7/2018 | Bly et al. |
| 10,016,613 B2 | 7/2018 | Kavounas |
| 10,076,656 B2 | 9/2018 | Dar et al. |
| 10,192,387 B2 | 1/2019 | Brinig et al. |
| 10,307,133 B2 | 6/2019 | Kaib |
| 10,463,867 B2 | 11/2019 | Kaib et al. |
| 10,589,110 B2 | 3/2020 | Oskin et al. |
| 10,599,814 B2 | 3/2020 | Landrum et al. |
| 10,940,323 B2 * | 3/2021 | Sullivan ................. A61B 5/363 |
| 2002/0181680 A1 | 12/2002 | Linder et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0144355 A1 | 6/2013 | Macho et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1 | 2/2014 | Cowan et al. |
| 2014/0070957 A1 | 3/2014 | Longinotti-Buritonil et al. |

(56) References Cited

U.S. PATENT DOCUMENTS

| | | |
|---|---|---|
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0161554 A1 | 6/2015 | Sweeney et al. |
| 2015/0297135 A1 | 10/2015 | Shoshani et al. |
| 2015/0328472 A1 | 11/2015 | Sullivan et al. |
| 2016/0004831 A1 | 1/2016 | Carlson et al. |
| 2016/0076175 A1 | 3/2016 | Rock et al. |
| 2016/0076176 A1 | 3/2016 | Rock et al. |
| 2016/0082277 A1 | 3/2016 | Foshee, Jr. et al. |
| 2016/0113581 A1 | 4/2016 | Amir et al. |
| 2016/0256104 A1 | 9/2016 | Romem et al. |
| 2016/0283900 A1 | 9/2016 | Johnson et al. |
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0162840 A1 | 6/2017 | Pendry |
| 2017/0278370 A1 | 9/2017 | Kaib et al. |
| 2017/0319862 A1 | 11/2017 | Foshee, Jr. et al. |
| 2017/0367591 A1 | 12/2017 | Jorgenseon |
| 2018/0116537 A1 | 5/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0243578 A1 | 8/2018 | Volosin |
| 2018/0361165 A1 | 12/2018 | Jaax et al. |
| 2019/0030352 A1 | 1/2019 | Sullivan et al. |
| 2019/0076666 A1 | 3/2019 | Medema |
| 2019/0116896 A1 | 4/2019 | Armour et al. |
| 2019/0321650 A1 | 10/2019 | Raymond et al. |
| 2020/0155826 A1 | 5/2020 | Kaib et al. |

FOREIGN PATENT DOCUMENTS

| | | |
|---|---|---|
| EP | 3434326 A1 | 1/2019 |
| JP | 4320257 B2 | 8/2009 |
| JP | 2014526282 A | 10/2014 |
| JP | 5963767 B2 | 8/2016 |
| WO | 1998039061 A2 | 9/1998 |
| WO | 2011146448 A1 | 11/2011 |
| WO | 2012064604 A1 | 5/2012 |
| WO | 2012151160 A1 | 11/2012 |
| WO | 2015056262 A1 | 4/2015 |

OTHER PUBLICATIONS

International Search Report and Written Opinion for PCT Application No. PCT/US2015/051726, dated May 20, 2016, European Patent Office, Rijswijk, 11 pages.

Klein, H. U., Goldenberg I., & Moss, A. J., Risk Stratification for Implantable Cardioverter Defibrillator Therapy: The Role of the Wearable Cardioverter-Defibrillator, Clinical update, European Heart Jounal, May 31, 2013, pp. 1-14, doi:10.1093/eurheartj/eht167, European Society of Cardiology.

LIFECOR LifeVest System Model WCD 3100 Operator's Manual, 2006, PN 20B0040 Rev FI, Zoll Lifecor Corporation, Pittsburgh, PA.

Heartstart MRx and XL AED Algorithm—Application Note, Jul. 2001, Edition 2 Phillips Healthcare, USA.

ZOLL LifeVest Model 4000 Patient Manual PN 20B0047 Rev B, (C) 2009-2012.

* cited by examiner

*SAMPLE COMPONENTS OF WEARABLE CARDIOVERTER DEFIBRILLATOR (WCD) SYSTEM*

SAMPLE COMPONENTS OF EXTERNAL DEFIBRILLATOR

*ELECTRODES & ECG SIGNALS ALONG MULTIPLE VECTORS*

WEARABLE CARDIOVERTER DEFIBRILLATOR (WCD) WITH POWER-SAVING FUNCTION

CROSS REFERENCES TO RELATED PATENT APPLICATIONS

This application is a continuation of U.S. patent application Ser. No. 15/715,550, filed on Sep. 26, 2017, which claims the benefit of U.S. Provisional Patent Application Ser. No. 62/404,158, filed on Oct. 4, 2016, the entire disclosures of which, as initially made, are hereby incorporated by reference.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim.

Some people have an increased risk of SCA. People at a higher risk include patients who have had a heart attack, or a prior SCA episode. A frequent recommendation is for these people to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart.

After being identified as having an increased risk of an SCA, and before receiving an ICD, these people are sometimes given a Wearable Cardioverter Defibrillator (WCD) system. (Early versions of such systems were called wearable cardiac defibrillator systems.) A WCD system typically includes a harness, vest, or other garment that the patient is to wear. The WCD system further includes electronic components, such as a defibrillator and electrodes, coupled to the harness, vest, or other garment. When the patient wears the WCD system, the external electrodes may then make good electrical contact with the patient's skin, and therefore can help determine the patient's ECG. If a shockable heart arrhythmia is detected, then the defibrillator delivers the appropriate electric shock through the patient's body, and thus through the heart.

To detect a shockable arrhythmia, a WCD system may perform computations on the patient's ECG signal. Typically, the more intensive the computations, the more reliable the detection result will be. Rhythm analysis algorithms can be computationally burdensome. For example, an algorithm proposed by Irusta et al. (A high-temporal resolution algorithm to discriminate shockable from nonshockable rhythms in adults and children, Resuscitation (2012)), involves a number of steps, some of which may include performing a Fast Fourier Transform (FFT) every 3.2 seconds.

Computations are not free, however. Computations are performed by machine operations of a processor of the WCD system. These machine operations require electrical current to be performed, and thus tax the stored energy of the battery accordingly. The more computations that are required, the more energy will be required from the battery. And FFTs require a lot of such computations. The more energy that is required from the battery, the more energy the battery needs to store from when it is put into service until it is switched out for recharging.

BRIEF SUMMARY

The present description gives instances of Wearable Cardioverter Defibrillator (WCD) systems, storage media that store programs, and methods, the use of which may help overcome problems and limitations of the prior art.

In embodiments, a WCD system has a processor that performs two different analyses to an ECG of the patient. A first-level analysis can be computationally economical, while a fuller second-level analysis can give shock/no-shock advice with more certainty. In some of these embodiments the second-level analysis of the ECG is performed only if the first-level analysis of the ECG detects a possible shockable condition. As such, the first-level analysis may operate as a gatekeeping function, often preventing the more computationally intensive second-level analysis from being performed.

An advantage can be that the WCD system needs to store less electrical charge, for powering the processor. In turn, this permits portions of the WCD system to be less bulky and weigh less.

These and other features and advantages of the claimed invention will become more readily apparent in view of the embodiments described and illustrated in the present disclosure, namely from the present written specification and the drawings.

DETAILED DESCRIPTION

As has been mentioned, the present description is about Wearable Cardioverter Defibrillator (WCD) systems, storage media that store programs, and methods. Embodiments are now described in more detail.

A wearable cardioverter defibrillator (WCD) system made according to embodiments has a number of components. These components can be provided separately as modules that can be interconnected, or can be combined with other components, etc.

Figure 1:
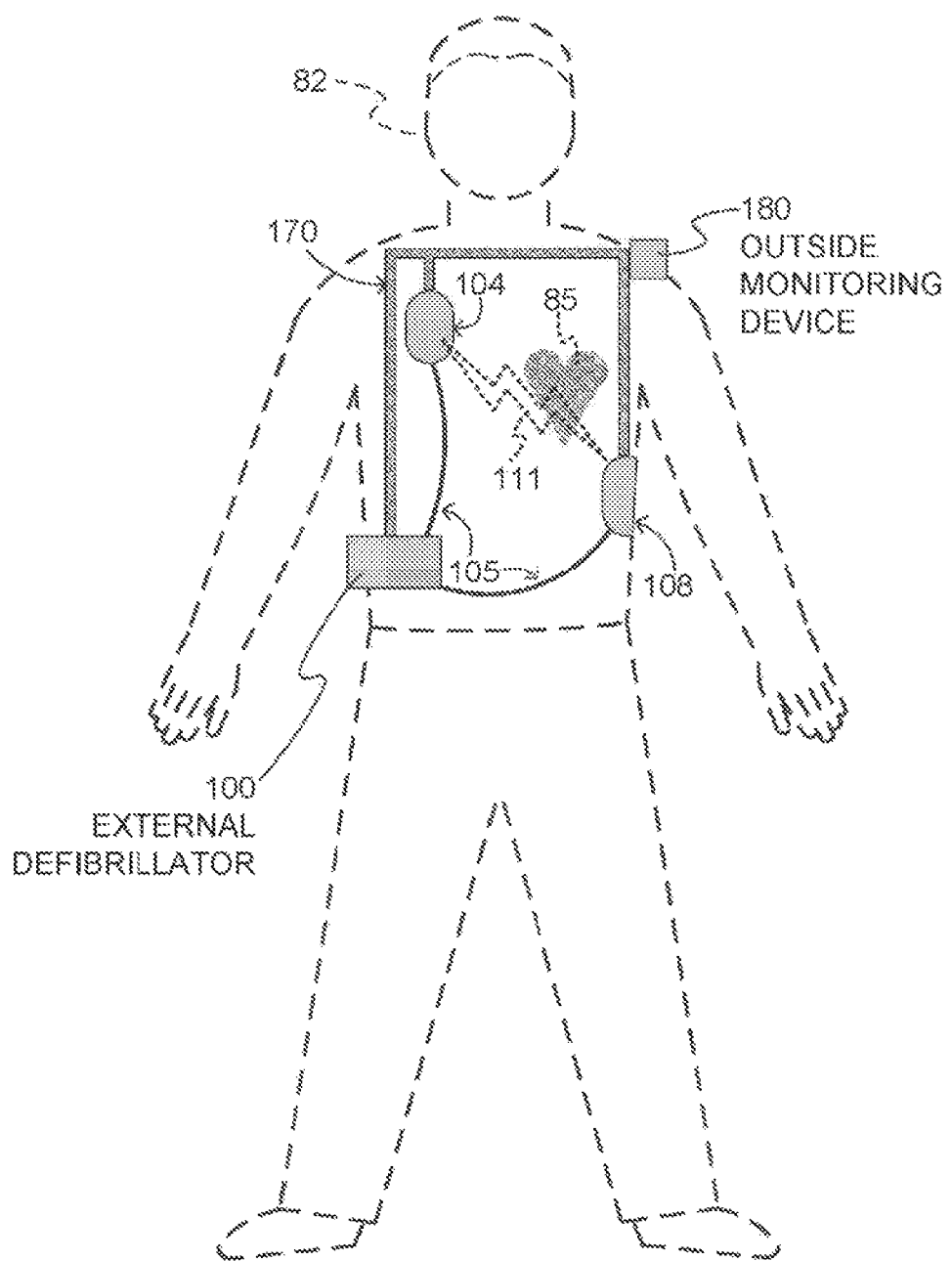
FIG. 1 is a diagram of components of a sample wearable cardioverter defibrillator (WCD) system, made according to embodiments.

FIG. 1 depicts a patient 82. Patient 82 may also be referred to as a person and/or wearer, since that patient wears components of the WCD system. Patient 82 is ambulatory, which means patient 82 can walk around and is not bedridden.

FIG. 1 also depicts components of a WCD system made according to embodiments. One such component is a support structure 170 that is wearable by patient 82. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to parallel articles of clothing. In embodiments, support structure 170 could include a harness, one or more belts or straps, etc. In such embodiments, such items can be worn by around the torso, hips, over the shoulder, etc. In embodiments, support structure 170 can include a container or housing, which can even be waterproof. In such embodiments, the support structure can be worn by being attached to the patient by adhesive material, for example as shown in U.S. Pat. No. 8,024,037. Support structure 170 can even be implemented as described for the support structure of US Pat. App. No. US 2017/0056682 A1, which is incorporated herein by reference. Of course, in such embodiments, the person skilled in the art will recognize that additional components of the WCD system can be in the housing of a support structure instead of attached externally to the support structure, for example as described in the 2017/0056682 document. There can be other examples.

A WCD system according to embodiments is configured to defibrillate a patient who is wearing it, by delivering an electrical charge to the patient's body in the form of an electric shock delivered in one or more pulses. FIG. 1 shows a sample external defibrillator 100, and sample defibrillation electrodes 104, 108, which are coupled to external defibrillator 100 via electrode leads 105. Defibrillator 100 and defibrillation electrodes 104, 108 can be coupled to support structure 170. As such, many of the components of defibrillator 100 could be therefore coupled to support structure 170. When defibrillation electrodes 104, 108 make good electrical contact with the body of patient 82, defibrillator 100 can administer, via electrodes 104, 108, a brief, strong electric pulse 111 through the body. Pulse 111, also known as shock, defibrillation shock, therapy or therapy shock, is intended to go through and restart heart 85, in an effort to save the life of patient 82. Pulse 111 can further include one or more pacing pulses, and so on.

A prior art defibrillator typically decides whether to defibrillate or not based on an ECG signal of the patient. However, external defibrillator 100 may initiate defibrillation (or hold-off defibrillation) based on a variety of inputs, with ECG merely being one of them.

Accordingly, it will be appreciated that signals such as physiological signals containing physiological data are obtained from patient 82. While the patient may be considered also a "user" of the WCD system, this is not a requirement. That is, for example, a user of the wearable cardioverter defibrillator (WCD) may include a clinician such as a doctor, nurse, emergency medical technician (EMT) or other similarly situated individual (or group of individuals). The particular context of these and other related terms within this description should be interpreted accordingly.

The WCD system may optionally include an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document. Device 180 may include one or more transducers or sensors that are configured to render one or more physiological inputs from one or more patient parameters that it senses.

Optionally, device 180 is physically coupled to support structure 170. In addition, device 180 can be communicatively coupled with other components, which are coupled to support structure 170. Such communication can be implemented by a communication module, as will be deemed applicable by a person skilled in the art in view of this description.

Figure 2:
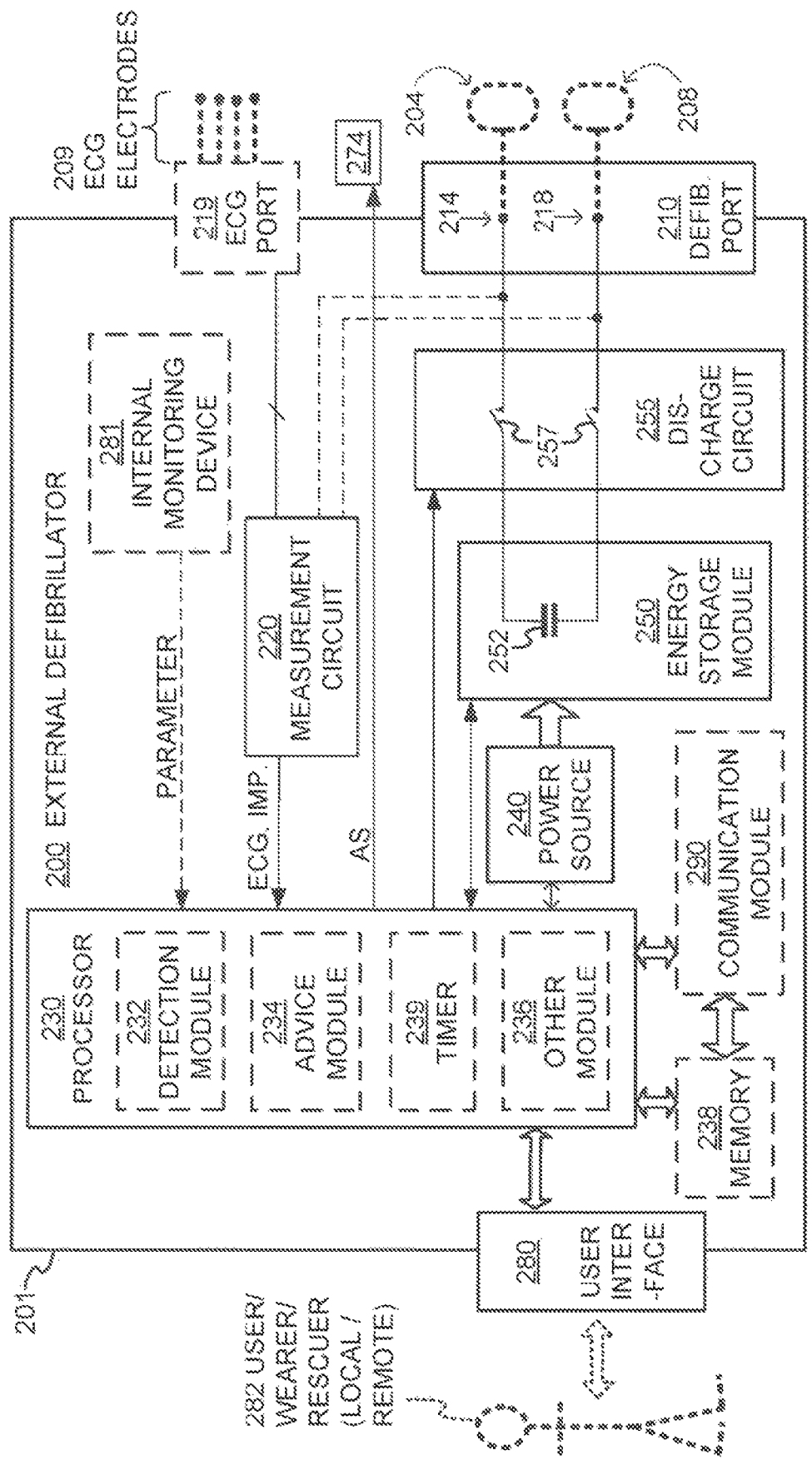
FIG. 2 is a diagram showing sample components of an external defibrillator, such as the one belonging in the system of FIG. 1, made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as patient 82 of FIG. 1. Defibrillator 200 may further include a user interface 280 for a user 282. User 282 can be patient 82, also known as wearer 82. Or user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible or tactile, for communicating to a user by outputting images, sounds or vibrations. Images, sounds, vibrations, and anything that can be perceived by user 282 can also be called human perceptible indications. There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds to warn bystanders, etc.

User interface 280 may further include input devices for receiving inputs from users. Such input devices may additionally include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which monitoring device can be done according to design considerations. Device 281 may include one or more transducers or sensors that are configured to render one or more physiological inputs from one or more patient parameters that it senses.

Patient parameters may include patient physiological parameters. Patient physiological parameters may include, for example and without limitation, those physiological parameters that can be of any help in detecting by the wearable defibrillation system whether the patient is in need of a shock, plus optionally their medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an $SpO_2$ sensor, and so on. In view of this disclosure, it will be appreciated that such sensors can help detect the patient's pulse, and can therefore also be called pulse detection sensors, pulse sensors, and pulse rate sensors. Pulse detection is also taught at least in Physio-Control's U.S. Pat. No. 8,135,462, which is hereby incorporated by reference in its entirety. In addition, a person skilled in the art may implement other ways of performing pulse detection. In such cases, the transducer includes an appropriate sensor, and the physiological input is a measurement by the sensor of that patient parameter. For example, the appropriate sensor for a heart sound may include a microphone, etc.

In some embodiments, the local parameter is a trend that can be detected in a monitored physiological parameter of patient 282. A trend can be detected by comparing values of parameters at different times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$ or $CO_2$; f) respiratory function, respiratory rate, etc.; g) motion, level of activity; and so on. Once a trend is detected, it can be stored and/or reported via a communication link, along perhaps with a warning. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor.

Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may include a motion detector. In embodiments, a motion detector can be implemented within monitoring device 180 or monitoring device 281. Such a motion detector can be configured to detect a motion event. In response, the motion detector may render or generate from the detected motion event a motion detection input that can be received by a subsequent device or functionality. A motion event can be defined as is convenient, for example a change in motion from a baseline motion or rest, etc. Such a motion detector can be made in many ways as is known in the art, for example by using an accelerometer. In such cases, the patient parameter is a motion, one of the transducers may include a motion detector, and the physiological input is a motion measurement.

System parameters of a WCD system can include system identification, battery status, system date and time, reports of self-testing, records of data entered, records of episodes and intervention, and so on.

Environmental parameters can include ambient temperature and pressure. Moreover, a humidity sensor may provide information as to whether it is likely raining. Presumed patient location could also be considered an environmental parameter. The patient location could be presumed if monitoring device 180 or 281 includes a GPS location sensor as per the above.

Defibrillator 200 typically includes a defibrillation port 210, such as a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in an energy storage module 250 that is described more fully later in this document. The electric charge will be the shock for defibrillation, pacing, and so on.

Defibrillator 200 may optionally also have an ECG port 219 in housing 201, for plugging in sensing electrodes 209, which are also known as ECG electrodes and ECG leads. It is also possible that sensing electrodes 209 can be connected continuously to ECG port 219, instead. Sensing electrodes 209 are types of transducers that can help sense an ECG signal, e.g. a 12-lead signal, or a signal from a different number of leads, especially if they make good electrical contact with the body of the patient. Sensing electrodes 209 can be attached to the inside of support structure 170 for making good electrical contact with the patient, similarly as defibrillation electrodes 204, 208.

Optionally a WCD system according to embodiments also includes a fluid that it can deploy automatically between the electrodes and the patient's skin. The fluid can be conductive, such as by including an electrolyte, for making a better electrical contact between the electrode and the skin. Electrically speaking, when the fluid is deployed, the electrical impedance between the electrode and the skin is reduced. Mechanically speaking, the fluid may be in the form of a low-viscosity gel, so that it does not flow away, after it has been deployed. The fluid can be used for both defibrillation electrodes 204, 208, and sensing electrodes 209.

The fluid may be initially stored in a fluid reservoir, not shown in FIG. 2, which can be coupled to the support structure. In addition, a WCD system according to embodiments further includes a fluid deploying mechanism 274. Fluid deploying mechanism 274 can be configured to cause at least some of the fluid to be released from the reservoir, and be deployed near one or both of the patient locations, to which the electrodes are configured to be attached to the patient. In some embodiments, fluid deploying mechanism 274 is activated prior to the electrical discharge responsive to receiving activation signal AS from processor 230 that is described more fully later in this document.

In some embodiments, defibrillator 200 also includes a measurement circuit 220, as one or more of its sensors or transducers. Measurement circuit 220 senses one or more electrical physiological signals of the patient from ECG port 219, if provided. Even if defibrillator 200 lacks ECG port 219, measurement circuit 220 can obtain physiological signals through nodes 214, 218 instead, when defibrillation electrodes 204, 208 are attached to the patient. In these cases, the physiological input reflects an ECG measurement. The parameter can be an ECG, which can be sensed as a voltage difference between electrodes 204, 208. In addition the parameter can be an impedance, which can be sensed between electrodes 204, 208 and/or the connections of ECG port 219. Sensing the impedance can be useful for detecting, among other things, whether these electrodes 204, 208 and/or sensing electrodes 209 are not making good electrical contact with the patient's body. These patient physiological signals can be sensed, when available. Measurement circuit 220 can then render or generate information about them as physiological inputs, data, other signals, etc. More strictly speaking, the information rendered by measurement circuit 220 is output from it, but this information can be called an input because it is received by a subsequent device or functionality as an input.

Defibrillator 200 also includes a processor 230. Processor 230 may be implemented in a number of ways. Such ways include, by way of example and not of limitation, digital and/or analog processors such as microprocessors and Digital Signal Processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

The processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also referred to as "software," generally provide functionality by performing methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as physiological inputs, data, or other signals, may be used by the VF detector to determine whether the patient is experiencing VF. Detecting VF is useful, because VF results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments, and determining whether a shock criterion is met. This may determine whether a possible or actual shockable condition exists or not. The determination can be made from a rhythm analysis of the captured ECG signal or otherwise.

In some embodiments, when the determination is to shock, an electrical charge is delivered to the patient. Delivering the electrical charge is also known as discharging. Shocking can be for defibrillation, pacing, and so on.

Processor 230 can further include a timer 239. Alternately, timer 239 can be provided as a separate module.

Processor 230 can include additional modules, such as other module 236, for other functions. In addition, if internal monitoring device 281 is indeed provided, it may be operated in part by processor 230, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, actions and/or methods to be performed, and/or the processor to cause other devices or components or blocks to perform such functions, operations, processes, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or stored there after it is received by defibrillator 200.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy storage capacitor, and so on. In some embodiments, power source 240 is controlled by processor 230. Appropriate components may be included to provide for charging or replacing power source 240.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

Defibrillator 200 moreover includes a discharge circuit 255. When the decision is to shock, processor 230 can be configured to control discharge circuit 255 to discharge through the patient the electrical charge stored in energy storage module 250. When so controlled, circuit 255 can permit the energy stored in module 250 to be discharged to nodes 214, 218, and from there also to defibrillation electrodes 204, 208, so as to cause a shock to be delivered to the patient. Circuit 255 can include one or more switches 257. Switches 257 can be made in a number of ways, such as by an H-bridge, and so on. Circuit 255 can also be controlled via user interface 280.

Defibrillator 200 can optionally include a communication module 290, for establishing one or more wired or wireless communication links with other devices of other entities, such as a remote assistance center, Emergency Medical Services (EMS), and so on. Module 290 may also include such sub-components as may be deemed necessary by a person skilled in the art, for example an antenna, portions of a processor, supporting electronics, outlet for a telephone or a network cable, etc. This way, data, commands, etc. can be communicated. The data can include patient data, event information, therapy attempted, CPR performance, system data, environmental data, and so on.

Defibrillator 200 can optionally include other components.

Returning to FIG. 1, in embodiments, one or more of the components of the shown WCD system have been customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. Such baseline physiological parameters can be used to customize the WCD system, in order to make its diagnoses more accurate, since the patients' bodies differ from one another. Of course, such parameters can be stored in a memory of the WCD system, and so on.

A programming interface can be made according to embodiments, which receives such measured baseline physiological parameters. Such a programming interface may input automatically in the WCD system the baseline physiological parameters, along with other data.

Figure 3:
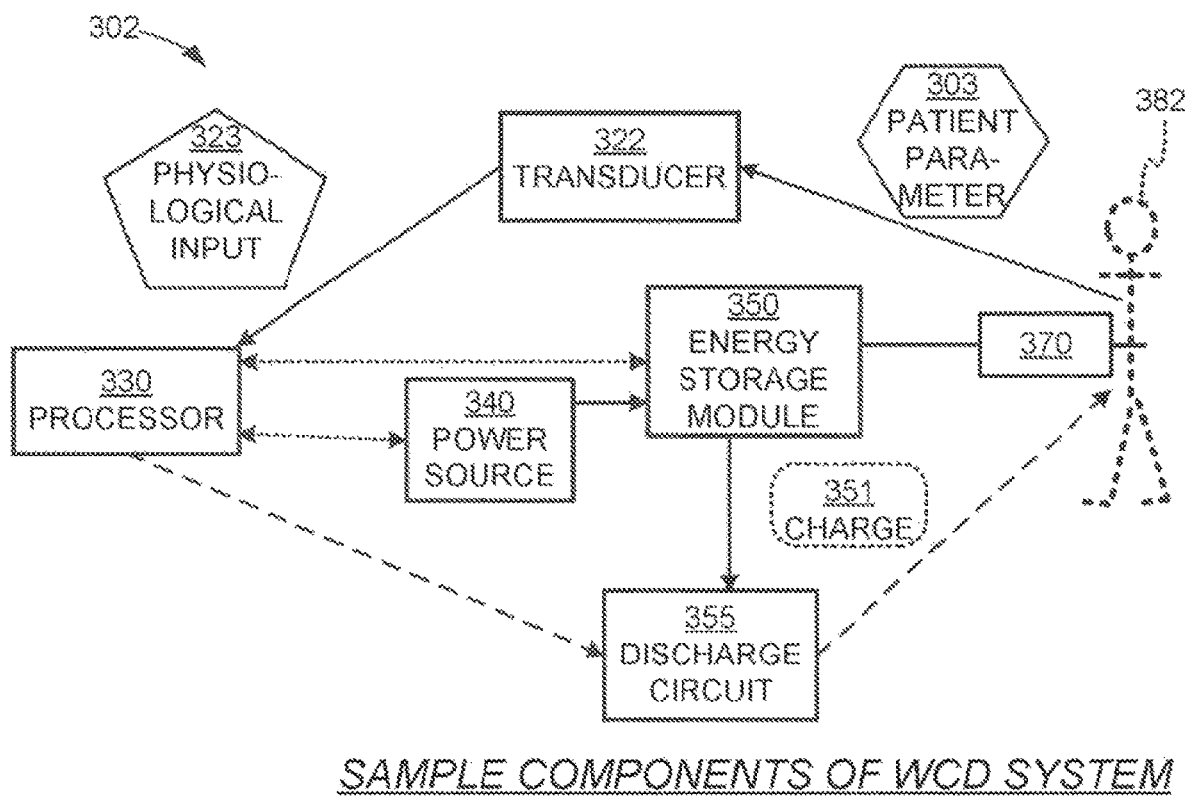
FIG. 3 is a diagram of sample components of a WCD system in relation to a patient according to embodiments.

Referring now to FIG. 3, in some versions or embodiments, a set of components 302 of a wearable cardioverter defibrillator (WCD), such as those mentioned above, are described in relation to a patient 382. For example, components 302 include a support structure 370 that is configured to be worn by patient 382, which can be made as support structure 170. Components 302 also include a power source 340, an energy storage module 350 that is configured to receive an electrical charge from power source 340 and to store the received electrical charge, and a discharge circuit 355 coupled to energy storage module 350, all made as described for power source 240, energy storage module 250 and discharge circuit 255, respectively.

Components 302 may further include a transducer 322 that can have ECG electrodes such as sensing electrodes 209. Transducer 322 can be configured to render, from a parameter 303 that is an Electrocardiogram (ECG) of patient 382, a physiological input 323 that includes ECG data of patient 382.

Components 302 may further include a processor 330, which can be made as described for processor 230. Processor 330 can be configured to perform analyses on physiological input 323, for example as described later in this document in more detail. Depending on the results of these analyses, processor 330 may control discharge circuit 355 to discharge the electrical charge 351 that is stored in energy storage module 350 through patient 382 so as to deliver a shock to patient 382 while support structure 370 is worn by patient 382.

In embodiments, components 302 may perform different types of analyses on physiological input 323. Examples are now described.

Figure 4:
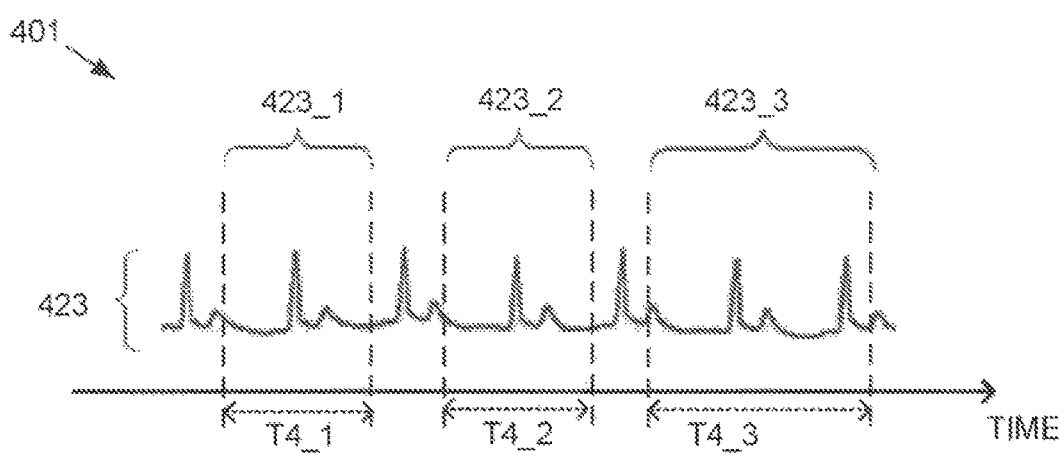
FIG. 4 is a time diagram of sample first, second and third ECG data of respectively a first, a second and a third portion of a physiological input of the patient, rendered according to embodiments.

Referring to FIG. 4, a time diagram 401 is shown, where sample ECG data 423 is plotted against a time axis. A first, a second, and a third portion of the physiological input are identified. In particular, the first portion includes first ECG data 423_1 from a first time segment T4_1, the second portion includes second ECG data 423_2 from a second time segment T4_2, and the third portion includes third ECG data 423_3 from a third time segment T4_3. Such time segments can also be called time intervals, and so on. Moreover, even though these portions of the ECG data are shown in the context of these time segments or intervals, there is no requirement that the ECG data has been stored already in a memory. Nor is there a requirement that the subsequently described analyses 541, 542 cannot be running continuously. In fact, such analyses can be running continuously, on ECG data that is running continuously. Nor is there a requirement that such time segments or intervals be defined, between moments in time for example. Rather, time segments or intervals are being used in this document only to provide a common denominator for comparing and contrasting analyses 541, 542 in terms of their complexity, intensiveness, the number of their machine operations, their energy consumption, etc.

It will be observed that, in this example of FIG. 4, the first time segment and the second time segment have equal durations. The third time segment, however, lasts longer than either the first time segment or the second time segment.

In addition, in this example of FIG. 4, none of the intervals is temporally contiguous with any of the others, although that could well happen. For example, the second time segment could follow immediately after the first time segment, and so on. Moreover, in this example of FIG. 4, none of the intervals overlaps any of the others, although that could well happen. For example, the second time segment could overlap with the first time segment at least in part, include all of the first time segment, be identical to it, and so on.

Possible analyses, decisions, and other actions by processor 330 are now described in more detail. In some embodiments, processor 330 may be able to perform a first-level analysis on a first portion of the physiological input, to detect whether or not a possible shockable condition exists. The first portion may include first ECG data 423_1, from first time segment T4_1.

In addition, processor 330 may be able to perform a second-level analysis on a second portion of the physiological input, to detect whether or not an actual shockable condition exists. The second portion may include second ECG data 423_2, from second time segment T4_2, or third ECG data 423_3, from third time segment T4_3, and so on. It will be further recognized that, if the intervals were to overlap, the first-level analysis and the second-level analysis of the ECG could be of the same ECG data at least in part.

Figure 5:
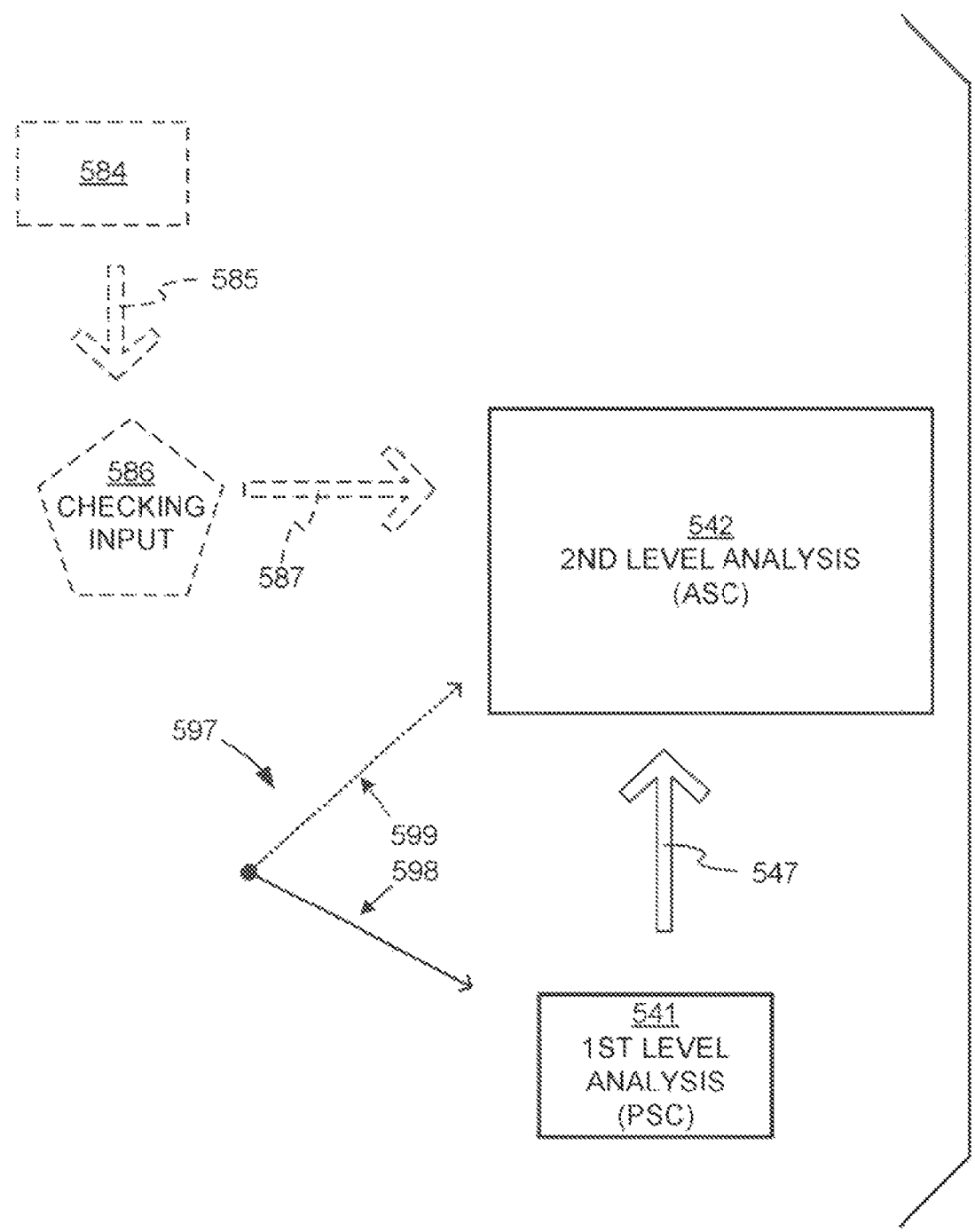
FIG. 5 is a diagram illustrating that at least two different types of analyses may be performed according to embodiments.

Referring now to FIG. 5, a set 597 of arrows 598, 599 illustrates a choice that at least two different types of analyses 541, 542 may be performed by processor 330 according to embodiments. It will be understood that this representation is the same regardless of whether analyses 541, 542 are performed by different computational modules or a single one.

In FIG. 5, solid arrow 598 points to a first-level analysis 541, which is to be performed to determine whether or not a Possible Shockable Condition (PSC) exists. Or, dotted arrow 599 points to a second-level analysis 542 alternately to first-level analysis 541. Second-level analysis 542 can be performed to determine whether or not an Actual Shockable Condition (ASC) exists. The actual shockable condition is generally different from the possible shockable condition, although that is not required.

In this representation, arrow 598 is solid, to indicate the present choice of set 597 in this example. These choices are thought of in the alternative, but this need not be the case. Both analyses could be running at some time, to compare their results.

First-level analysis 541 is different from second-level analysis 542, in that these analyses may be performed differently, and/or be performed to detect shockable conditions that are different. In some embodiments first-level analysis 541 has a higher sensitivity than second-level analysis 542. Indeed, first-level analysis 541 can be designed to have a high sensitivity so that there is a very high probability that it will detect any rhythm that might require the patient to be shocked. In addition, in some embodiments, second-level analysis 542 has a higher specificity than first-level analysis 541. By way of background, in medical diagnosis, test sensitivity is the ability of a test to correctly identify those with a problem, which is also called the true positive rate. On the other hand, test specificity is the ability of the test to correctly identify those without the problem, which is also called the true negative rate. Put another way, if a test is highly sensitive and the test result is negative, one can be nearly certain that they don't have the problem. A highly sensitive test thus helps rule out the problem, when its result is negative.

In embodiments, second-level analysis 542 is more computationally intensive than first-level analysis 541. This is conceptually hinted at, in this particular single instance of FIG. 5, by drawing box 542 as larger than box 541. Of course, the relative scale of boxes 541 and 542 is not intended to convey how much more computationally simpler process 541 over process 542, and so on.

In embodiments where second-level analysis 542 is more computationally intensive than first-level analysis 541, the processor consumes more electrical power in performing second-level analysis 542 than first-level analysis 541. Since power is found by dividing energy over time, in such embodiments performing second-level analysis 542 may require the processor to consume more energy than performing first-level analysis 541, if the first time segment had an equal duration with the second time segment. As already mentioned previously, this supposition that the first time segment would have an equal duration with the second time segment is made simply so as to equalize the denominators of the consumed energy to arrive at consumed electrical power, and does not require that the ECG data is cast in time intervals as opposed to running continuously, or that these time segments actually have equal durations.

For describing the above-mentioned computationally intensiveness or its opposite (simplicity), a computational statistic may be considered. The computational statistic can be the number of machine operations by processor 330 for processing a set of ECG data, divided by the duration during which this set of ECG data was acquired. As such, in embodiments, more machine operations per the duration of the second time segment can be required for performing the second-level analysis, than the machine operations per the duration of the first time segment required for performing the first-level analysis. In another way of saying this, performing the second-level analysis can require more machine operations by processor 330 than performing the first-level analysis, if the first time segment had an equal duration with the second time segment.

Embodiments or versions may save on computations, which can save electrical power for the wearable system. Indeed, microprocessor power consumption is related to the number of computations required. Moreover, a microprocessor that is used only lightly, i.e. for fewer computations, can be clocked at a slower rate to further reduce power consumption. Or, for intermittent computations according to embodiments, such a microprocessor can be put to sleep in a low-power state the majority of the time and woken up only when there are computations to be done. In embodiments, the computations are completed quickly, and the microprocessor spends most of its time in a dormant state. It is understood that, in this disclosure, words like dormant may connote pauses in activity that are long, or much shorter than are typically associated with chip states, etc.

In some embodiments, discharge circuit 355 is controlled to discharge stored electrical charge 351 through the patient responsive to thus detecting that the possible shockable condition exists or that the actual shockable condition exists. Some embodiments can be even more sophisticated, as will be seen later in this document.

In embodiments, second-level analysis 542 may provide analyses of higher certainty than first-level analysis 541. In fact, this can be supported by second-level analysis 542 being more computationally intensive than first-level analysis 541.

In some embodiments, first-level analysis 541 is running routinely, while second-level analysis 542 is running only occasionally, or when triggered. The preference for running first-level analysis 541 over second-level analysis 542 over the long term may conserve power.

Triggering may take place as a result of an outcome of the first-level analysis. Alternately, triggering may take place from a different kind of event, such as a checking input being received upon being generated, regardless of whether or not the first-level analysis was being performed at the time, or what its outcome is. Examples of such triggering are now described, and it will be understood that these examples are not mutually exclusive.

In some embodiments, second-level analysis 542 is performed responsive to a checking input 586 being received, for example by processor 330. In FIG. 5, arrow 587 is drawn to suggest that checking input 586 triggers the performance of second-level analysis 542. A number of possible devices 584 can generate checking input 586 according to arrow 585. For one example, device 584 can be a motion detector that is configured to generate checking input 586 responsive to a motion of the patient that is detected by the motion detector. This could be generated, for instance, upon detecting that the previously moving patient has suddenly stopped moving.

For another example, device 584 can be a timer 239 configured to generate checking input 586 at a preset time. The preset time can be programmed to be any suitable time. For instance, the preset time is such that the checking input is generated at substantially periodic time segments, e.g. such as every 30 min, 10 min, 1 min, 20 sec, etc. Or, the preset time is when a predefined time period has elapsed during which the second-level analysis has not been performed.

In some embodiments, device 584 can be a leads-off module. The leads-off module may be configured to detect when one or more of the electrodes have lost contact with patient 82, and to generate checking input 586 responsive to so detecting.

In some embodiments, device 584 can be a noise detector that is configured to detect when there is a certain amount of electrical noise, for example in an ECG signal, in a detected impedance, and so on. In such embodiments, the noise detector can be configured to generate checking input 586 responsive to so detecting.

In some embodiments checking input 586 can be generated if a condition is sustained for a predetermined duration. Such a condition can be as mentioned in this document, for example VT, VF, SVT (Supraventricular Tachycardia), bradycardia, asystole, noise, leas off, or other.

In some embodiments, first-level analysis 541 is performed, and second-level analysis 542 is further performed responsive detecting, by first-level analysis 541, that the possible shockable condition exists. This is indicated in FIG. 5 by arrow 547. In such embodiments it can be said that first-level analysis 541 performs a function of gatekeeping, or functions as a gatekeeper. The gatekeeping function results in power savings from not having to process as much, where deemed as not needed. In such embodiments, the discharge circuit can be controlled to thus discharge the stored electrical charge only responsive to detecting that the actual shockable condition exists, but not simply if the possible shockable condition exists.

Of course, all previously mentioned combinations are possible. In this case, second-level analysis 542 will be performed after first-level analysis 541. Analysis 542 can be performed on subsequent ECG data, or even on the same ECG data as analysis 541, for example if the ECG data has been stored and so on.

If an actual shocking condition is not detected to exist by second-level analysis 542, a number of operations may be performed afterwards. For example first-level analysis 541 may be repeated, and then repeated again, and so on, so as not to delay any VT/VF detection time. It is also possible to perform neither analysis for a preset pause time, to further save power. Again, in a number of embodiments, so as not to delay any VT/VF detection time, if any such pauses of first-level analysis 541 are indeed performed, they are preferably of a short duration so they are not clinically significant in the context of the overall detection—unless other detection provisions have been made.

Various ways of establishing such gatekeeping functions are described in this document. In general, it is preferred that the gatekeeper is designed to be computationally simple so that it can run on a low-power microcontroller.

One way to implement a gatekeeper that is computationally simple is to have it process a single ECG channel or vector. While a WCD system according to embodiments may be able to acquire data simultaneously from multiple ECG channels, the gatekeeper may process data from only one channel, or a reduced number of channels, so that it can execute first-level analysis 541 on a small, low-power microcontroller. Second-level analysis 542, however, can use more channels to achieve a more reliable rhythm analysis, even at the expense of computational complexity. An example is now described.

Figure 6:
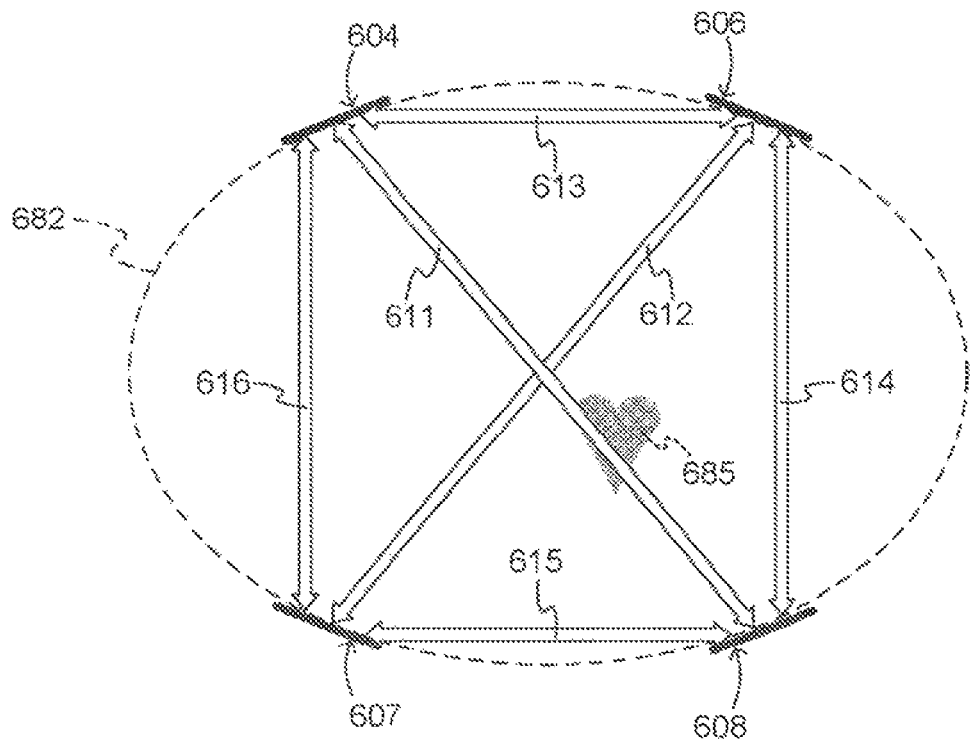
FIG. 6 is a conceptual diagram for illustrating how a WCD system can use electrodes to acquire ECG signals along different vectors according to embodiments.

FIG. 6 is a conceptual diagram for illustrating how electrodes of a WCD system may capture ECG signals along different channels or vectors according to embodiments. A section of the torso of a patient 682 is shown. Patient 682 has heart 685. There are four electrodes 604, 606, 607, 608, attached to the torso. Any pair of these four electrodes may define a vector or channel, across with an ECG signal may be measured. The four electrodes 604, 606, 607, 608 therefore can define six vectors, across which six respective ECG signals 611, 612, 613, 614, 615, 616 can be captured. In FIG. 6 it will be understood that electrodes 604, 606, 607, 608 are drawn on the same plane for simplicity, while that is not necessarily the case. Accordingly, the vectors of ECG signals 611, 612, 613, 614, 615, 616 are not necessarily on the plane of the diagram, either.

Figure 7:
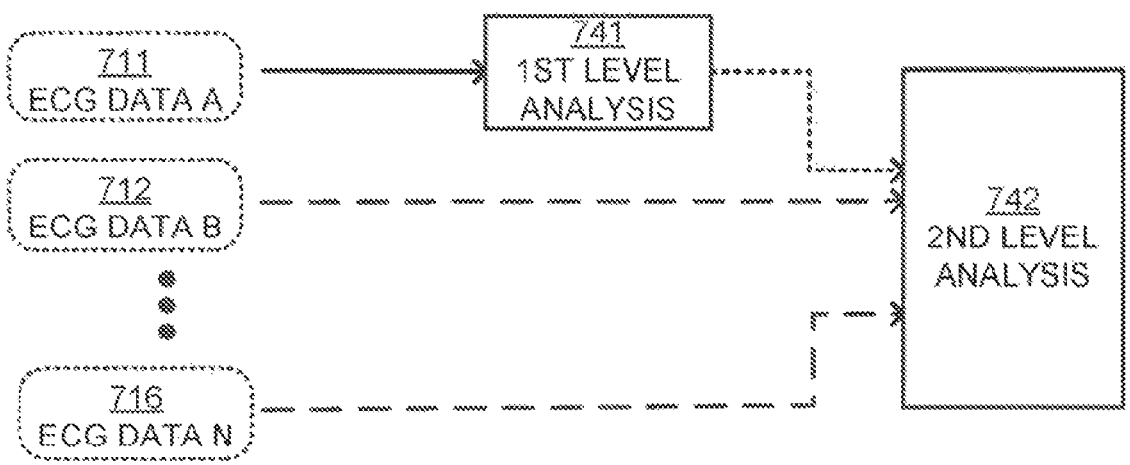
FIG. 7 is a diagram indicating that ECG signals acquired along different vectors may be subjected to different types of analyses according to embodiments.

FIG. 7 is a diagram indicating that ECG signals acquired along different vectors, such as by the configuration of FIG. 6, may be subjected to different types of analyses according to embodiments. A first-level analysis 741 may include analyzing the ECG data of a first number of the ECG channels. Here, first-level analysis 741 includes analyzing ECG Data A 711 of a single channel. In other words, that first number of the ECG channels is just one.

A second-level analysis 742 may include analyzing the ECG data of a second number of the ECG channels that is larger than that first number. Here, second-level analysis 742 includes analyzing ECG Data B 712, . . . , ECG Data N 716 of multiple channels. In fact, in embodiments, second-level analysis 742 may further include analyzing ECG Data A 711 of the earlier-mentioned channel.

In some embodiments, the first level analysis is from only one of the ECG channels, which has been designated as the best available channel. In particular, the ECG data can be acquired from at least a first and a second distinct ECG channels. As some time, the first ECG channel can be designated as the best ECG channel, and the first-level analysis may include analyzing the ECG data of only the ECG channel that has been thus designated as the best ECG channel, in other words of only the first channel. Responsive to the second-level analysis, the second ECG channel may later become designated as the best ECG channel, in other words, the second ECG channel may be deemed to be providing more reliable data. After the second-level analysis is performed, the first-level analysis can be performed again, and it may include analyzing the ECG data of only the ECG channel that has been thus designated as the best ECG channel. In this latter case, however, the "best channel" designation has shifted to the second channel in this example.

In some embodiments, the first-level analysis includes extracting a numerical statistic from the first ECG data. In such embodiments, the possible shockable condition is detected if a value of the statistic is beyond a threshold value TH, either by exceeding the threshold value TH or by being lower than the threshold value TH. It will be understood that, and as will be seen in more detail below, for the specific case of tachycardia detection, the numerical statistic would be derived from a detected heart rate, and would exceed a high threshold. Moreover, the numerical statistic that represents the heart rate might need to be lower than a low threshold in some instances. Examples are now described.

Figure 8:
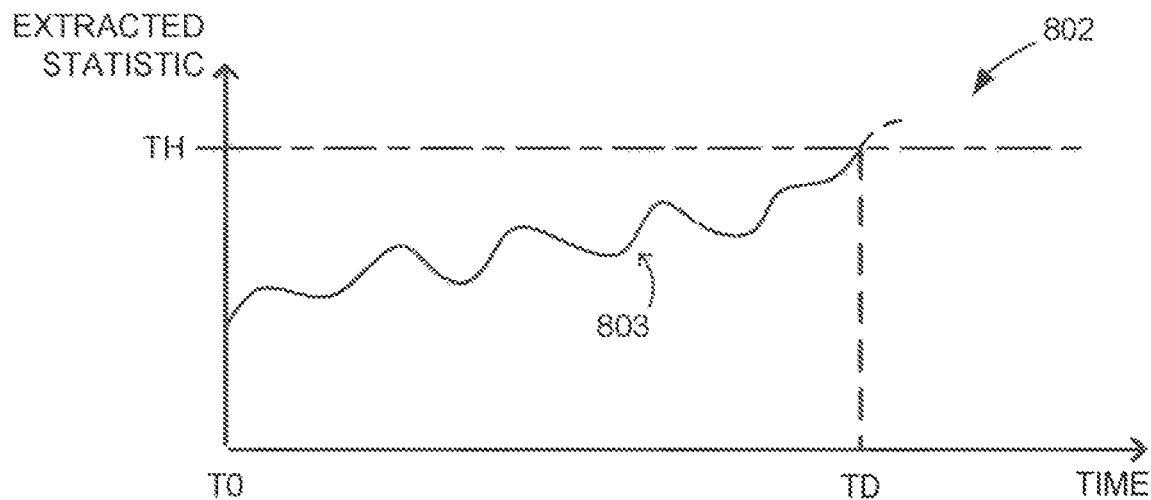
FIG. 8 is a time diagram that represents sample detection of a possible shockable condition when an extracted statistic exceeds a threshold, according to embodiments.

FIG. 8 is a time diagram 802. The value of the extracted statistic is plotted on the vertical axis against a time axis. The plot is a line 803 that starts at time T0, at which time line 803 has a value less than that of a threshold value TH. At time TD, however, line 803 exceeds threshold value TH, which means detection. A number of values can be used as the extracted statistic.

When the first-level analysis is used as a gatekeeping function, it does not necessarily require a high specificity. This is because the subsequent second-level analysis can be made more reliable, by performing a full rhythm analysis before a final shock decision is made. Of course, if the first-level gatekeeper is not to have a high specificity, there will likely be instances where the gatekeeper flags a non-shockable rhythm as being potentially shockable, and the subsequent full second-level analysis would discern correctly that the patient does not need to be shocked. Those cases can be considered as internal false alarms within the WCD system. These are to be distinguished from false alarms where the WCD system is preparing to shock the patient, unless the latter acts to prevent it. Rather, in cases of those internal false alarms, the patient need not become alarmed or even notified for that matter. Even if the patient is notified, that can be done in a context of an assurance.

In embodiments, the extracted statistic of FIG. 8 is a detected heart rate. When the first-level analysis is used as a gatekeeping function, then the gatekeeper can simply be a heart rate detector.

In some embodiments, the heart rate detector detects when the heart rate is too high. The gatekeeper could flag a rhythm as being potentially shockable if the detected heart rate exceeds a threshold value TH; for such an example the value of TH could equal 135 BPM+/−10%. BPM is a frequency measurement for the heart rate, standing for "beats" per minute. Shockable rhythms, such as ventricular fibrillation (VF) and high-rate ventricular tachycardia (VT), both exhibit a heart rate greater than 135 BPM. Patients wearing a WCD system who do not need a defibrillation shock would not normally have a heart rate greater than 135 BPM.

It is possible that some non-shockable rhythms might occasionally have a heart rate higher than 135 BPM. For example, supraventricular tachycardia (SVT) can occasionally exceed 135 BPM and it should not be shocked. It is also possible that noise might cause the heart rate detector to erroneously measure a heart rate>135 BPM when the actual heart rate is lower. Both of these situations can be accommodated by the WCD system according to embodiments because, in some of these embodiments, the full rhythm analysis algorithm has the ability to distinguish noise and SVT from a shockable rhythm. As long as the gatekeeper does not detect a heart rate greater than 135 BPM very often, then a substantial power savings can be achieved, while the patient may be continuously monitored so that any shockable rhythms are detected.

In other embodiments, the heart rate detector detects when the heart rate is too low. For example, it might be desirable to detect bradycardia, even though it is not shockable. A bradycardia condition can be detected if a value of the heart rate is less than a threshold value TH of 40 BPM+1-10%. Other provisions can be made for detecting asystole.

Still referring to FIG. 8, in some embodiments, the processor is configured to set or adjust the value TH of the threshold adaptively, so as to individualize the WCD for the patient. There are discrepancies among patients, both clinical and in terms of their daily activities. Indeed, patients are not alike, their daily activities are not alike, and their physiological responses to their daily activities are not uniform. As such, the same settings might cause the possible shockable condition PSC to be detected more often in some patients than others. If there are too many internal false alarms, it may be beneficial to raise the threshold. A young patient who is likely to tolerate a high heart rate could also benefit from a higher threshold. On the other hand, an older, medically fragile patient may benefit from a lower threshold to ensure that no tachyarrhythmias are missed.

As such, the value TH of the threshold may set initially, and then adjusted in a number of ways. One such way is according to how often the possible shockable condition PSC is detected. In embodiments where arrow 547 is implemented, this may further set according to how often the more computationally intensive second-level analysis is performed. Depending on the purpose of the adjustment, there are different examples of how the value TH of the threshold can be set or adjusted.

Some examples account for an initial setting, and proceed with adjusting. The gatekeeper could begin with a relatively low threshold, thereby triggering a full analysis relatively often. After repeated full analyses yield a no-shock result at, say, 140 BPM, the WCD system might conclude that it is safe to increase the threshold value to 150 BPM. In this scheme an upper threshold limit of perhaps 180 BPM would be set to prevent the possibility of missing a dangerous arrhythmia. Conversely, if the threshold is set at 150 BPM and the patient never reaches that rate, the device may conclude that it is safe to decrease the threshold value.

In some embodiments, the threshold value can be set such that the possible shockable condition is detected on an expected number of occasions per day. To achieve a specific number of full analyses per day the WCD system can track the patient's heart rate over time. Over that time, the WCD system can develop an estimate of the distribution of the patient's heart rate in a typical day. This distribution could be used to set a heart rate threshold at a value that can be calculated to trigger approximately one full analysis per hour. A full analysis would still be triggered by the gatekeeper based on the patient's heart rate, as described hereinabove, but the heart rate threshold would be adjusted so that the desired number of full analyses is performed per day. Executing a full analysis approximately periodically may provide extra reassurance that a lethal arrhythmia has not been overlooked. The period may be a suitable amount of time, e.g. once every minute.

Other examples account for challenging situations that may be encountered. For instance, the power source may include a battery, and the threshold value can be set based on a charge level of the battery. As such, perhaps a higher threshold will cause fewer computation-intensive and power-consuming second-level analyses to be performed, so as to conserve battery power. This approach may slightly raise the risk of missing an important arrhythmia, but that may be better than letting the battery run dead with consequent total failure of the WCD system.

In some embodiments, the threshold value is set depending on one or more results of the second-level analysis. For instance, the threshold value can be set based on a number of actual shockable conditions detected by a plurality of iterations of the second-level analysis. Moreover, the full, second-level analysis may be able to measure more characteristics than just a shock/no shock conclusion, and diagnose a patient condition. For example, the full analysis may have the additional ability to: distinguish cardiac signals from noise, to distinguish supraventricular rhythms from ventricular rhythms, and to measure the duration of self-terminating arrhythmias. For example, if a non-sustained run of VT is detected (which is very dangerous for the patient), the gatekeeper threshold value might be lowered to provide increased vigilance. On the other hand, if the patient is prone to supraventricular tachycardia (which has a high rate but is relatively benign), the threshold value might be raised to avoid consuming too much power. If the gatekeeper is tripped due to noise, the threshold value might also be raised.

As seen above, the defibrillator of FIG. 2 includes memory 238. In fact, a WCD system may include one or more memories. Ordinarily the ECG data streaming from the transducer, which can be the electrodes, is first stored in one of the memories, and then it is analyzed. In some embodiments, the gatekeeper may operate on continuously streaming digital data of the ECG, only in a single direction. In some embodiments, the first-level analysis can be performed on the first ECG data as the first ECG data is streaming from the transducer, and without the streaming first ECG data having been stored in any of the one or more memories. In contrast, ECG data can be saved for the full analysis, and the saved ECG data can be partitioned into segments for analysis. Segmental analysis can be beneficial because the saved ECG data can be analyzed forwards and/or backwards, whereas continuously streaming data can only be processed in one direction. In addition, the full second-level analysis can make as multiple passes through each segment of ECG data as necessary, whereas continuously streaming data can only be handled in a single pass. An example of a multiple pass algorithm to be used in the full analysis might be a QRS detector that first finds all of the ECG peaks in a segment of ECG data, then sorts the ECG peaks by amplitude, and retains all of the peaks that are greater than 25% of the maximum amplitude (>0.25 $A_{max}$). As such, having the gatekeeper operate on continuously streaming digital data of the ECG may reduce memory requirements.

The gatekeeping function could also be based on functions other than heart rate. For example, and as mentioned above, in some embodiments a WCD system can further include a detector configured to generate a detector signal. Many possible detectors are described above, such as a motion detector, detector of patient physiological conditions, detector of environmental conditions, a timer, and so one. In such embodiments, the first-level analysis may include analyzing ECG data, while the second-level analysis includes analyzing ECG data and the detector signal.

Another possible gatekeeping function might be the bWT function described by Irusta. This function yields a low value for signals with tall, narrow QRS complexes (which do not need to be shocked), and a higher value for signals with wide, fast QRS complexes like VT and VF (which do need to be shocked). The gatekeeper could also use an RMS measurement, a Peak-Peak measurement or other parameter as part of its initial rhythm assessment.

The gatekeeping function may also include an assessment of the patient activity level. This assessment could be made directly based on an accelerometer signal (to detect movement) or it could be based on a measurement that indirectly indicates patient motion, such as an impedance waveform measurement or a common mode voltage measurement. The gatekeeper may be able to reduce how often it falsely triggers a full analysis by taking into account patient activity. A patient who is moving under their own accord generally does not require a defibrillation shock.

The gatekeeping function could also include a combination of functions, such as a linear combination of heart rate and bWT. Such an algorithm might have more discriminating power than a single function alone, invoking a full analysis less often. On the other hand, a more complicated (and more discriminating) gatekeeper may cause the low-power microcontroller to consume more power.

The gatekeeper might also detect whether an electrode or electrode lead has become disconnected from the patient. Although this is not a potentially shockable event, the patient does need to be alerted so that they can reconnect the electrode/lead. The main processor would have the task of giving an audible and/or visual alert to the patient to let them know that corrective action is needed.

In some embodiments, the processor includes different computational modules for the different analyses of the ECG data. An example is now described.

Figure 9:
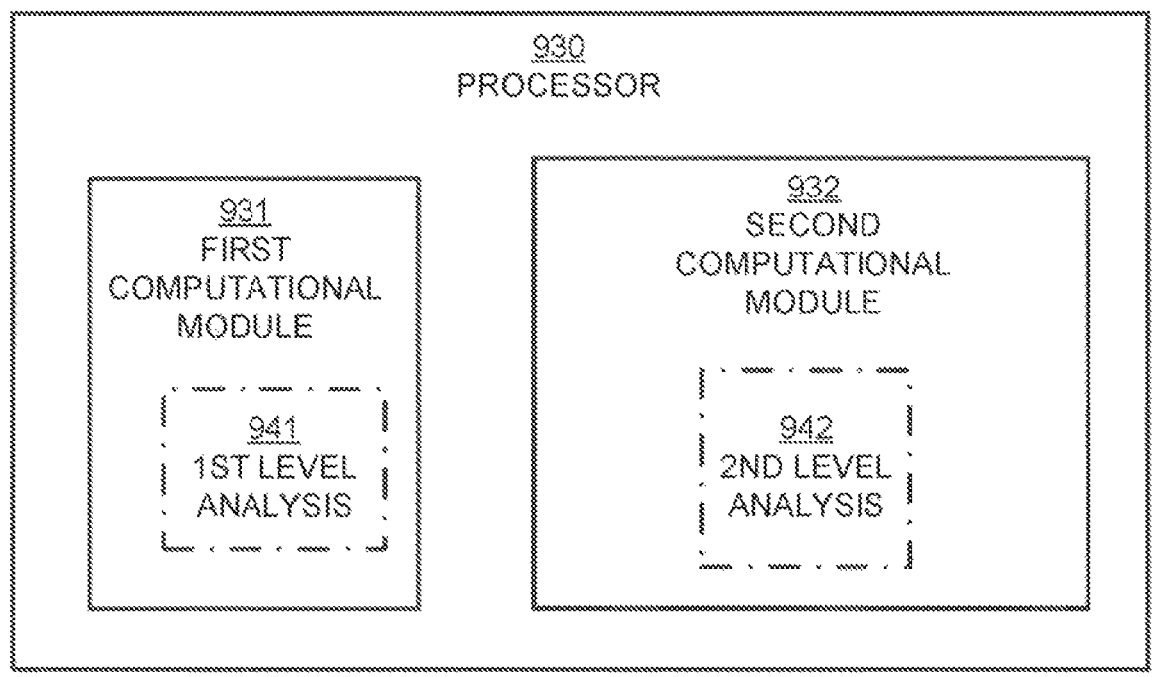
FIG. 9 is a block diagram of a sample processor of a WCD system according to embodiments, in which the processor includes different computational modules for the different analyses of the ECG data.

FIG. 9 shows a processor 930, which could be processor 230, 330, etc. Processor 930 includes a first computational module 931, which is configured to perform a first-level analysis 941. First-level analysis 941 can be as described above for first-level analysis 541. Processor 930 also includes a second computational module 932, which can be configured to perform a second-level analysis 942. Second-level analysis 942 can be as described above for second-level analysis 542.

Second computational module 932 can be distinct from first computational module 931. For example, first computational module 931 and second computational module 932 could be implemented in distinct cores of a multi-core processor. In such embodiments, the multi-core processor can be implemented by a single chip.

For another example, first computational module 931 and second computational module 932 could be implemented in distinct chips. In particular, first computational module 931 can be implemented by a first chip. The low-power microcontroller has sufficient bandwidth to perform an initial gatekeeping function.

In addition, second computational module 932 can be implemented by a second chip that is distinct from the first chip. This second chip can be thought of as the main microprocessor. A good candidate can be a processor with high computational bandwidth, even if not very power efficient. That is because, in some embodiments, this second chip is woken up only when the gatekeeper detects a possible shockable condition, such as a potentially shockable rhythm. A benefit of thinking this second chip as the main microprocessor is that, in some embodiments, many of its other tasks will not be performed while the WCD system is performing only the first-level analysis.

In embodiments, second computational module 932 is not performing second-level analysis 942 at a time when first computational module 931 is performing first-level analysis 941. Advantageously, at such times second computational module 932 may be in a dormant state, such as standby or OFF, which results in power consumption that is substantially reduced or nil. Second computational module 932 can be, however, in an awake state that is distinct than the dormant state when second computational module 932 is performing second-level analysis 942.

First computational module 931 can be made to have sufficient bandwidth to perform the gatekeeping function. Second computational module 932 can be woken up when triggered for second-level analysis 942. Examples of that were described above at least with reference to FIG. 5.

In such embodiments of separate chips, in order to optimize overall power consumption, more or less complexity can be allocated between the first-level analysis of the gatekeeping function and the second-level analysis. A more complicated gatekeeper will consume more power in the low-power microcontroller, but it may wake up the main processor less often.

In other embodiments, the processor has a chip that includes a single computational module for performing the different analyses of the ECG data. An example is now described, where the gatekeeping function runs in a processor that could be the main microprocessor.

Figure 10:
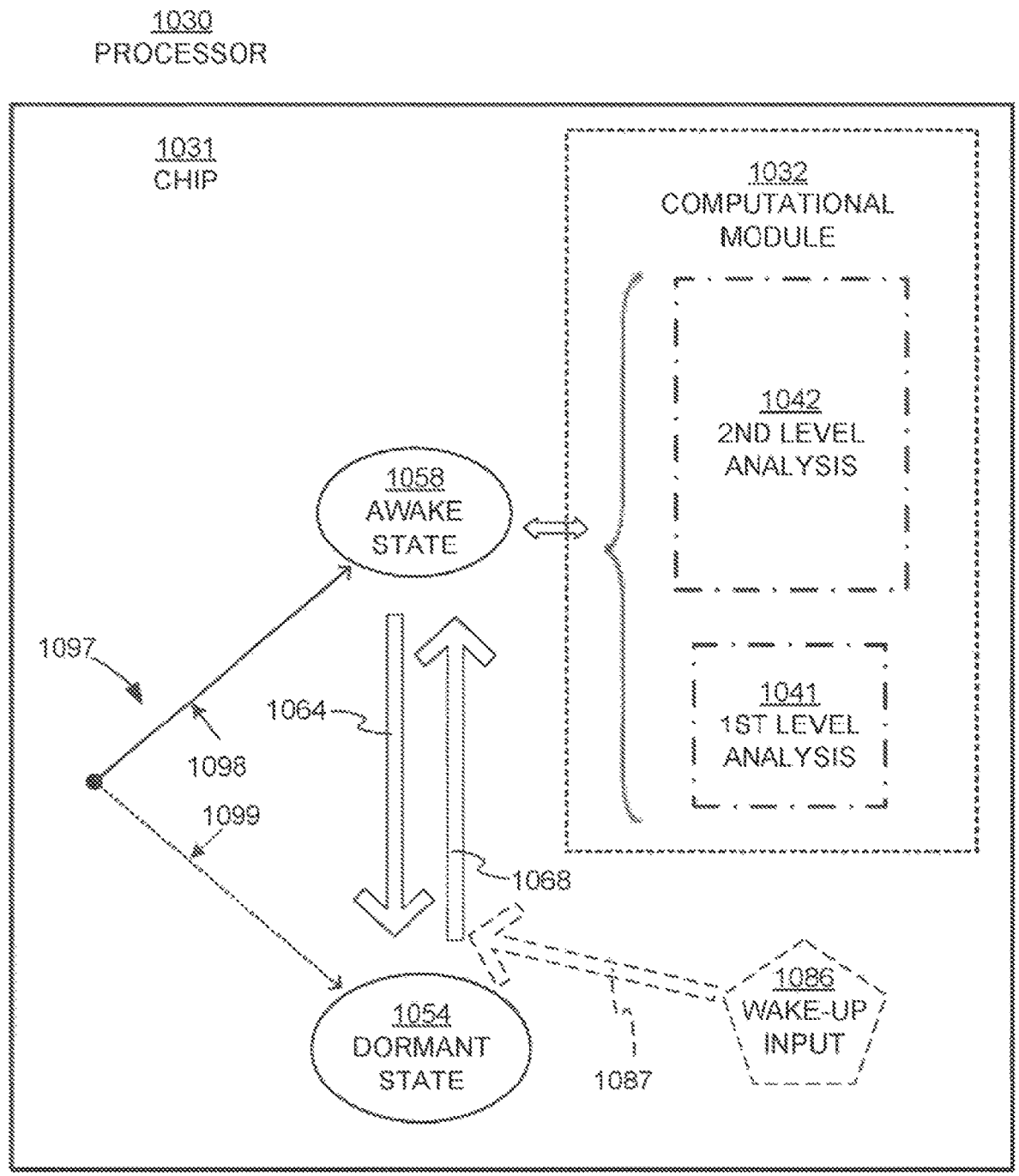
FIG. 10 is a block diagram of sample components of a chip of a processor of a WCD system according to embodiments, in which the chip can operate at different states depending on whether or not a single computational module is analyzing the ECG data.

FIG. 10 shows a chip 1031 that can include an integrated circuit (IC). Chip 1031 is part of a processor 1030, which could be as described for processor 230, 330, etc. Chip 1031 includes, among other components, a single computational module 1032. In some embodiments, computational module 1032 can be considered to be the same as, coextensive with, chip 1031 and in fact the entire processor 1030.

A set 1097 of arrows 1998, 1099 illustrates a choice that at chip 1031 can be in different states. In this representation, arrow 1098 is solid, to indicate the present choice of set 1097 in this example. Computational module 1032 can be configured to operate in an awake state 1058, when computational module 1032 performs either a first-level analysis 1041 or a second-level analysis 1042. First-level analysis 1041 and second-level analysis 1042 can be as described above for first-level analysis 541 and second-level analysis 542 respectively. When in awake state 1058, computational module 1032 may be drawing different amounts of power depending on which analysis it is performing.

Or, as indicated by a dotted arrow 1099, computational module 1032 can be configured to operate in a dormant state 1054 when computational module 1032 performs neither first-level analysis 1041 nor second-level analysis 1042. Dormant state 1054 is different from awake state 1058. Dormant state 1054 can be a standby state, an OFF state, and so on. Of course, and as mentioned above, the WCD system can pause this way from operating at least first-level analysis 1041 only judiciously. Indeed, pausing first-level analysis 1041 could delay detecting a tachycardia.

Chip 1031 consumes a high amount of power when computational module 1032 operates in awake state 1058, while it consumes a low amount of power when in dormant state 1054. The low amount of power is lesser than the high amount of power, which results in energy savings. Plus, while in awake state 1058, chip 1031 can be expending more power for performing analysis 1042 than analysis 1041. One reason can be a higher clock speed, because the calculations are more.

Computational module 1032 can be further configured to transition between awake state 1058 and dormant state 1054, and back again. For example, computational module 1032 may transition from awake state 1058 to dormant state 1054 according to an arrow 1064. This transition may be responsive to the possible shockable condition or the actual shockable condition not being detected, plus other factors such as passage of time, this having happened multiple times, and so on.

In addition, computational module 1032 may transition from dormant state 1054 to awake state 1058 according to an arrow 1068. This transition may be responsive to a wake-up input 1086 received according to an arrow 1087. What was written previously about checking input 586 may be applied also for creating wake-up input 1086, similarly or analogously. For example, a motion detector can be configured to generate wake-up input 1086 responsive to a motion of the patient that is detected by the motion detector, and so on.

For another example, a timer can be configured to generate wake-up input 1086 at a preset time. For instance, the preset time can be such that the wake-up input is generated at substantially periodic time segments, for example 3 times per hour. Or, the preset time can be when a predefined time period has elapsed during which computational module 1032 has been operating in dormant state 1054.

It will be appreciated that combinations of the above embodiments are also possible. For example, in the embodiment of FIG. 9, both computational modules may be put to a dormant state, with module 931 performing first-level analysis 941 only occasionally, and module 932 performing second-level analysis 942 even less frequently, except as other planning dictates for various conditions, some of which have already been discussed.

In some embodiments, the processor has a clock speed. That clock speed can be faster when second-level analysis 542 is performed than when first-level analysis 541 is performed. The higher clock speed can accommodate the more operations needed, and can result in more power being consumed. It will be recognized that this higher clock speed can be implemented in embodiments described above.

An operational example is now described, for showing many possible embodiments.

Figure 11:
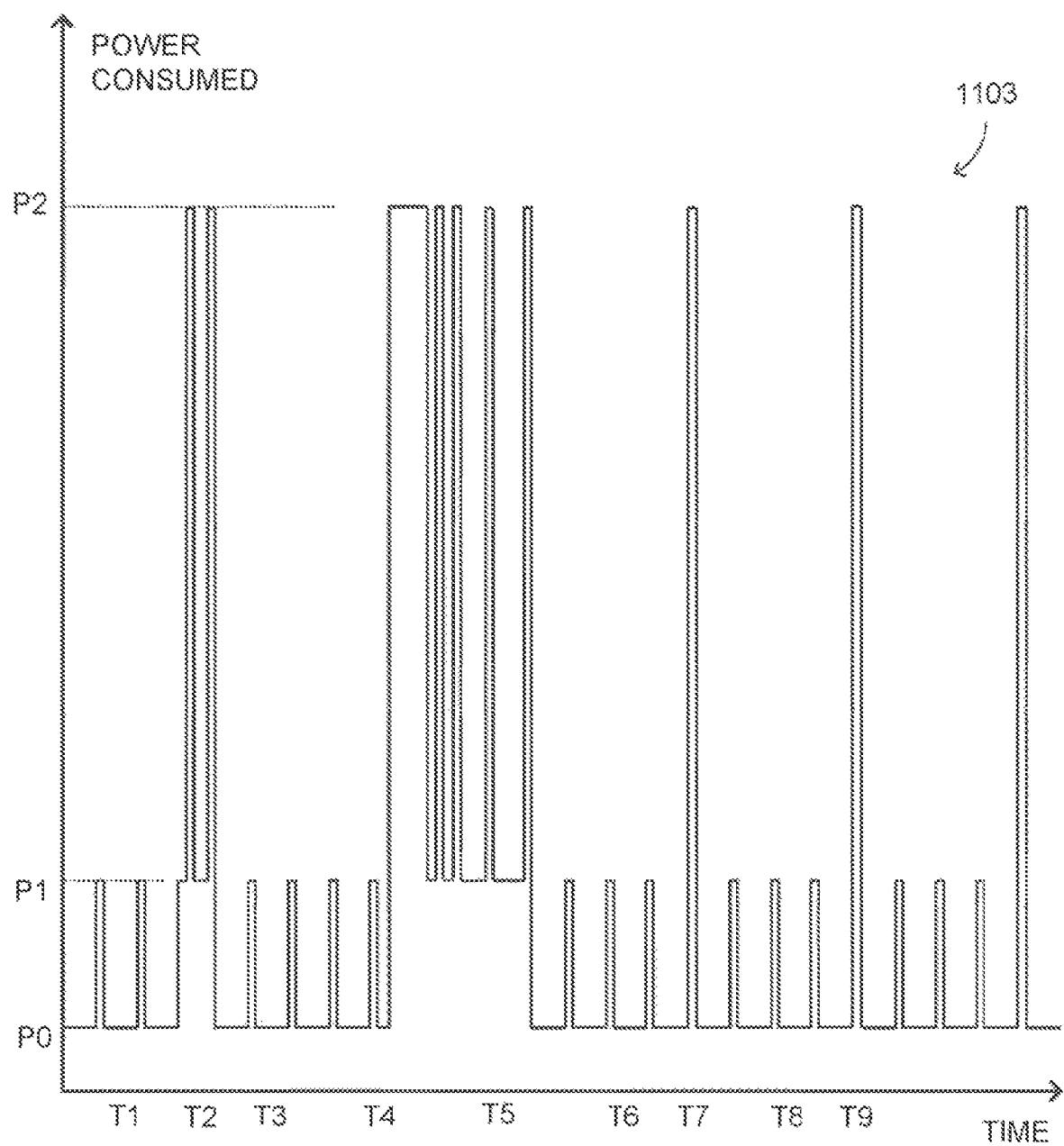
FIG. 11 is a time diagram showing a sample plot of power consumption over time for a processor of a WCD system according to embodiments.

FIG. 11 is a diagram that shows a sample plot 1103 of power consumed over time for a processor of a WCD system according to embodiments. It will be appreciated that plot 1103 is possible in various embodiments, for example where one chip or two separate chips are used for the computational modules, and so on.

In FIG. 11, the processor consumes power P0 when none of the analyses are performed, power P1 when only the first-level analysis is being performed, and power P2 when the second-level analysis is being performed. Power P2 is larger than power P1, but the diagram is not to scale. Moreover, in this example there are long pauses where power P0 is consumed. In some embodiments these pauses are short. In other embodiments, there are no such pauses and only power P1 or P2 is consumed.

In FIG. 11, the total energy consumed is the area under plot 1103. It will be appreciated that this is much less than for a processor that performs a full, second-level analysis all the time. In the latter case, the power consumed would be the area under line P2.

Various times are indicated for plot 1103. At time T1, the processor is in a regular monitoring pattern. In particular, the monitor could be mostly dormant, and only occasionally performing the gatekeeping function. As such, the consumed power occasionally jumps from P0 to P1, and then back. It will be appreciated that the processor spends a lot less time at P1 than at P0.

At time T2, the gatekeeping function has detected a possible shockable condition. As such, a full analysis is performed, which is why the consumed power jumps to P2. The full analysis indicates that the actual shockable condition does not exist, which was therefore an internal false alarm. The processor continues the gatekeeping function, and then checks again with a full analysis. Again, the actual shocking condition does not exist. At time T3, the processor returns to its regular monitoring pattern, assured that the internal false alarm of T2 is not a problem.

The regular monitoring pattern of time T3 is interrupted at time T4 by a triggering event, as described in connection with FIG. 5. Accordingly, direct full analysis is performed and is continued for some time.

At time TS, the full second-level analysis is paused, with the processor resuming only the gatekeeping function. The full analysis is repeated, but at increasing intervals as confidence in the well-being of the patient is restored.

Then the processor returns to its regular monitoring pattern, with occasional gatekeeping functions during time T6, followed by routine full second-level analysis at time T7. In this instance, the full second-level analysis was triggered only by a routine periodic checking input 586. The pattern of times T6, T7 is repeated at times T8, T9, and so on.

Saving on power consumption may also reduce the needed size of a WCD system. Indeed, a WCD system generally requires a minimum operating time during which there will be no changing or recharging the battery. Such a minimum operating time can be, say, 24 hours. The size of the battery required to achieve this operating time depends on the product power consumption. The battery is typically one of the larger components of a WCD system. The physical size of a WCD system is important for patient acceptance since the WCD system must be carried everywhere the patient goes.

The devices and/or systems mentioned in this document perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs.

Methods are now described.

Figure 12:
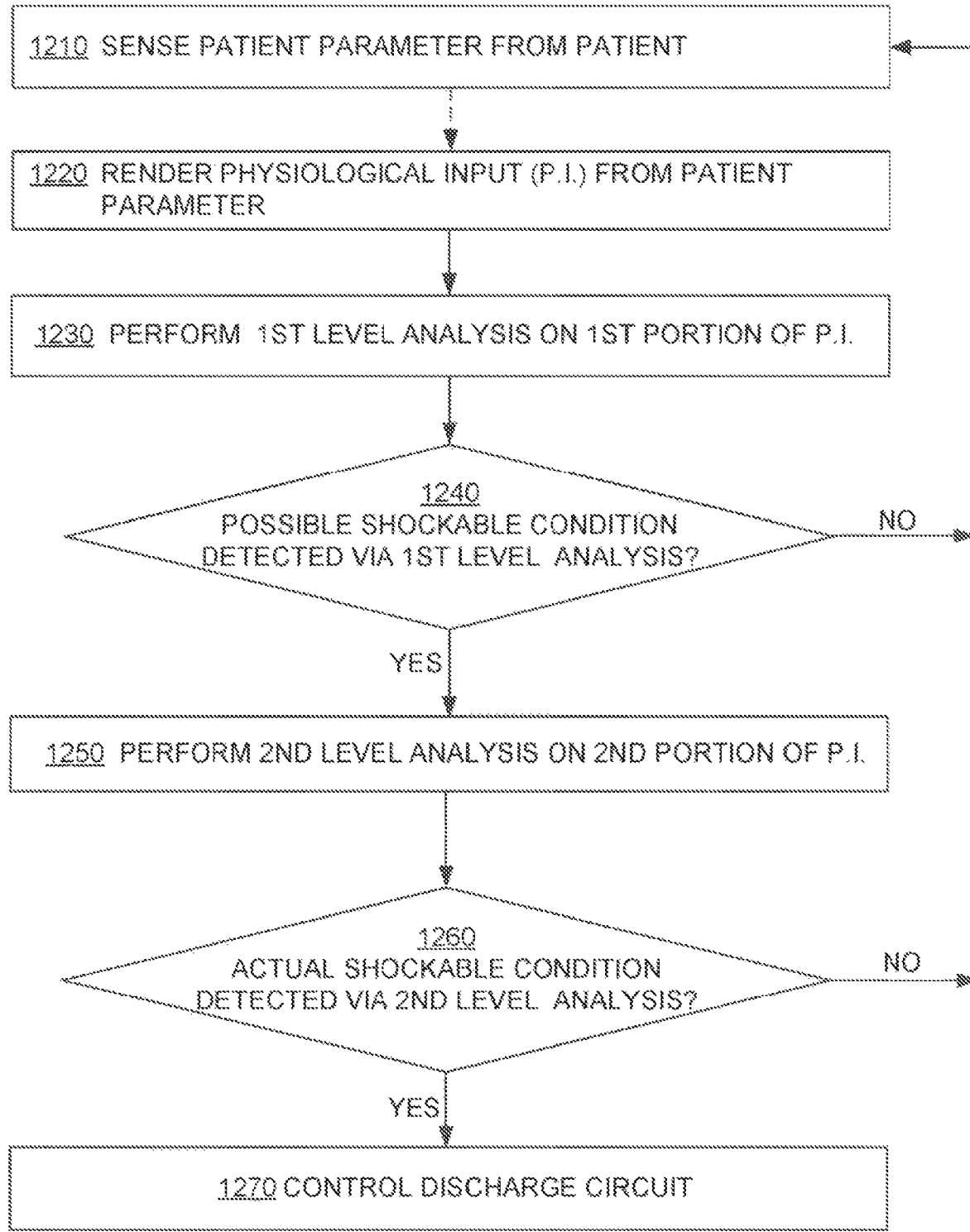
FIG. 12 is a flowchart for illustrating methods according to embodiments.

FIG. 12 shows a flowchart 1200 for describing methods according to embodiments. According to an operation 1210, a patient parameter can be sensed. The patient parameter can be an ECG of the patient.

According to another operation 1220, a physiological input (P.I.) may be rendered by the transducer from the sensed patient parameter. The physiological input may include ECG data of the patient.

According to another operation 1230, a first-level analysis may be performed on a first portion of the physiological input, to detect whether or not a possible shockable condition exists. The first portion may include first ECG data from a first time segment, and the first-level analysis may be as described for first-level analysis 541.

If at operation 1230 it is determined that the possible shockable condition does not exist then, according to a subsequent operation 1240, execution may return to operation 1210. Else, a subsequent operation 1250 takes place responsive to detecting, by the first-level analysis of operation 1230, that the possible shockable condition exists.

According to operation 1250 then, a second-level analysis is performed on a second portion of the physiological input, to detect whether or not an actual shockable condition exists. The second portion may include second ECG data from a second time segment. The second-level analysis may be such that performing the second-level analysis requires more machine operations by the processor than performing the first-level analysis of operation 1230, if the first time segment had an equal duration with the second time segment. In some embodiments, the second-level analysis may as described for second-level analysis 542.

If at operation 1250 it is determined that the actual shockable condition does not exist then, according to a subsequent operation 1260, execution may return to operation 1210. Else, a subsequent operation 1270 takes place responsive to detecting, by the second-level analysis of operation 1250, that the actual shockable condition exists.

According to operation 1270 then, a discharge circuit is controlled to discharge a stored electrical charge through the patient, so as to deliver a shock to the patient while the support structure is worn by the patient.

In normal operation of some embodiments, the gatekeeper function of operations 1230 and 1240 would evaluate the patient's ECG and wake up the main processor only when a full rhythm analysis is necessary or when other patient action is required. When the patient experiences a shockable rhythm the system would operate like this:

The gatekeeper function monitors the ECG;

the gatekeeper function detects a potentially shockable rhythm;

the gatekeeper function wakes up the main processor;

the main processor performs a full rhythm analysis, possibly also using an expanded number of channels; and if the full rhythm analysis indicates that a shock is required, then the main processor alerts the patient that a shock is about to be delivered, it stores ECG data to document the event, and it delivers the shock, optionally having alerted the patient and given the patient the chance to avert the shock.

In the methods described above, each operation can be performed as an affirmative step of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description. Anything written in the background section of this document is not, and should not be taken as, an acknowledgement or any form of suggestion that such is already known in the art, except where it is expressly pointed out. Plus, any reference to any prior art in this description is not, and should not be taken as, an acknowledgement or any form of suggestion that such prior art forms parts of the common general knowledge in any country or any art.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

In this description a single reference numeral may be used consistently to denote a single item, aspect, component, or process. Moreover, a further effort may have been made in the drafting of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

This disclosure is meant to be illustrative and not limiting on the scope of the following claims. The claims of this document define certain combinations and subcombinations of elements, features and steps or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

The embodiments of the invention in which an exclusive property or privilege is claimed are defined as follows:

1. A wearable cardioverter defibrillator (WCD) system, comprising:
   a support structure configured to be worn by a patient;
   an energy storage module configured to store an electrical charge;
   a discharge circuit coupled to the energy storage module;
   a transducer configured to render, from a sensed Electrocardiogram (ECG) of the patient, a physiological input that includes ECG data of the patient; and
   a processor configured to:
   perform a first-level analysis on a first portion of the physiological input to detect whether or not a possible shockable condition exists, the first portion including first ECG data from a first time segment,
   perform, responsive to detecting by the first-level analysis that the possible shockable condition exists, a second-level analysis on a second portion of the physiological input to detect whether or not a shockable condition exists, the second portion including second ECG data from a second time segment, in which the second-level analysis is different from the first-level analysis, and performing the second-level analysis requires the processor to consume more energy than performing the first-level analysis if the first time segment had an equal duration with the second time segment, and
   control, responsive to detecting that the shockable condition exists, the discharge circuit to discharge the stored electrical charge through the patient so as to deliver a shock to the patient while the support structure is worn by the patient.

2. The WCD system of claim 1, in which
the first-level analysis has a higher sensitivity than the second-level analysis.
3. The WCD system of claim 1, in which
the second time segment has a different time duration than the first time segment.
4. The WCD system of claim 1, in which
the second time segment overlaps with the first time segment at least in part.
5. The WCD system of claim 1, in which
the second-level analysis is performed responsive to a checking input being received.
6. The WCD system of claim 5, further comprising:
a motion detector configured to generate the checking input responsive to a motion of the patient that is detected by the motion detector.
7. The WCD system of claim 5, further comprising:
a timer configured to generate the checking input at a preset time.
8. The WCD system of claim 5, further comprising:
an electrode; and
a leads-off module configured to detect when the electrode has lost contact with the patient, and to generate the checking input responsive to so detecting.
9. The WCD system of claim 5, further comprising:
a noise detector configured to generate the checking input in response to detecting a noise reaching a threshold.
10. The WCD system of claim 1, in which if the shocking condition is not detected to exist, the first-level analysis is then repeated.
11. The WCD system of claim 1, in which
if the shocking condition is not detected to exist, neither the first level analysis nor the second-level analysis is then performed for a preset pause time.
12. The WCD system of claim 1, in which
the ECG data is acquired from a plurality of ECG channels,
the first-level analysis includes analyzing the ECG data of a first number of the ECG channels, and
the second-level analysis includes analyzing the ECG data of a second number of the ECG channels that is larger than the first number.
13. The WCD system of claim 1, in which
the ECG data is acquired from at least a first and a second ECG channels, the first ECG channel is designated as a selected ECG channel,
the first-level analysis includes analyzing the ECG data of only the selected ECG channel,
the second ECG channel becomes designated as a selected ECG channel responsive to the second-level analysis, and
after the second-level analysis is performed, the first-level analysis is performed again and includes analyzing the ECG data of only the second ECG channel that has been designated as the selected ECG channel.
14. The WCD system of claim 1, in which
the first-level analysis includes extracting a numerical statistic from the first ECG data, and
the possible shockable condition is detected if a value of the statistic is beyond a threshold value.
15. The WCD system of claim 14, in which
the statistic includes a heart rate.
16. The WCD system of claim 14, in which
the statistic includes a heart rate, and
the possible shockable condition is detected if a value of the heart rate exceeds a threshold value of 135 BPM+/−10%.
17. The WCD system of claim 14, in which
the statistic includes a heart rate, and
the possible shockable condition is detected if a value of the heart rate is less than a threshold value of 40 BPM+/−10%.
18. The WCD system of claim 14, in which
the processor is configured to set or adjust the threshold value adaptively.
19. The WCD system of claim 1, in which
the first-level analysis is performed on the first ECG data as the first ECG data is streaming only in a single direction.
20. The WCD system of claim 1, further comprising:
one or more memories, and
in which the first-level analysis is performed on the first ECG data as the first ECG data is streaming from the transducer, and without the streaming first ECG data having been stored in any of the one or more memories.
21. The WCD system of claim 1, further comprising:
a detector configured to generate a detector signal, and
in which the first-level analysis includes analyzing ECG data, while
the second-level analysis includes analyzing ECG data and the detector signal.
22. The WCD system of claim 1, in which
the processor includes
a first computational module configured to perform the first-level analysis, and a second computational module distinct from the first computational module,
the second computational module configured to perform the second-level analysis.
23. The WCD system of claim 22, in which
the first computational module and the second computational module are implemented in distinct cores of a multi-core processor, in which the multi-core processor is implemented by a single chip.
24. The WCD system of claim 22, in which
the first computational module is implemented by a first chip, and
the second computational module is implemented by a second chip that is distinct from the first chip.
25. The WCD system of claim 22, in which
the second computational module is not performing the second-level analysis at a time when the first computational module is performing the first-level analysis.
26. The WCD system of claim 22, in which
the second computational module is
in a dormant state when the first computational module is performing the firstlevel analysis, but
in an awake state distinct than the dormant state when the second computational module is performing the second-level analysis.
27. The WCD system of claim 1, in which
the processor has a chip that includes a computational module, and
the computational module is configured to operate in one of:
an awake state when the computational module performs either the first-level analysis or the second-level analysis, the chip consuming a high amount of power when the computational module operates in the awake state, and
a dormant state different from the awake state when the computational module performs neither the first-level analysis nor the second-level analysis, the chip consuming a low amount of power when in the dormant state, the low amount of power lesser than the high amount of power.

28. The WCD system of claim 27, in which
the computational module is further configured to transition from the awake state to the dormant state responsive to the possible shockable condition or the shockable condition not being detected.

29. The WCD system of claim 27, in which
the computational module is further configured to transition from the dormant state to the awake state responsive to a received wake-up input.

30. The WCD system of claim 1, in which
the processor has a clock speed, and
the clock speed is faster when the second-level analysis is being performed than when the first-level analysis is being performed.

* * * * *